United States Patent
Goffer et al.

(10) Patent No.: US 10,226,395 B2
(45) Date of Patent: Mar. 12, 2019

(54) LOCOMOTION ASSISTING DEVICE AND METHOD

(71) Applicant: ReWalk Robotics Ltd., Yokneam (IL)

(72) Inventors: Amit Goffer, Kiryat Tivon (IL); Chaya Zilberstein, Zikhron-Yaacov (IL)

(73) Assignee: REWALK ROBOTICS LTD., Yokneam, Illit (IL)

( * ) Notice: Subject to any disclaimer, the term of this patent is extended or adjusted under 35 U.S.C. 154(b) by 663 days.

(21) Appl. No.: 13/900,570

(22) Filed: May 23, 2013

(65) Prior Publication Data

US 2013/0261513 A1    Oct. 3, 2013

Related U.S. Application Data

(62) Division of application No. 13/735,160, filed on Jan. 7, 2013, now Pat. No. 8,905,955, which is a division
(Continued)

(51) Int. Cl.
*A61H 3/00* (2006.01)
*B25J 9/00* (2006.01)
(Continued)

(52) U.S. Cl.
CPC ........... *A61H 3/00* (2013.01); *A61H 1/0255* (2013.01); *A61H 1/0266* (2013.01); *A61H 3/008* (2013.01);
(Continued)

(58) Field of Classification Search
CPC .... A61F 5/0102; A61F 5/0123; A61F 5/0125; A61F 5/0127; A61F 5/013
See application file for complete search history.

(56) References Cited

U.S. PATENT DOCUMENTS 4,697,808 A * 10/1987 Larson ................. A61F 5/0102
                                                                    482/4
5,662,693 A    9/1997 Johnson et al.
(Continued)

FOREIGN PATENT DOCUMENTS

EP          2349121 A2    8/2011
WO    WO-2006/078871      7/2006
(Continued)

OTHER PUBLICATIONS

International Search Report of PCT/IL2009/000978 dated Apr. 5, 2010.
(Continued)

*Primary Examiner* — LaToya M Louis
(74) *Attorney, Agent, or Firm* — Cooley LLP

(57) ABSTRACT

An exoskeleton bracing system includes: a trunk support for affixing to the trunk of a disabled person and leg braces for connecting to the legs of the person, each leg brace including limb segment braces. Motorized joints are adapted to provide relative angular movement between the limb segment braces of the leg braces and between the leg braces and the trunk support. One or more ground force sensors are designed to sense ground force exerted on each of the leg braces. The system also includes a controller for receiving sensed signals from said one or more ground force sensors, with an algorithm for identifying a stance from the sensed signals and, based on the identified stance, actuating the motorized joints to perform an action relating to a mode of locomotion selected from a set of predefined actions corresponding to the identified stance.

5 Claims, 14 Drawing Sheets

Related U.S. Application Data of application No. 13/350,852, filed on Jan. 16, 2012, now Pat. No. 8,348,875, which is a division of application No. 12/250,155, filed on Oct. 13, 2008, now Pat. No. 8,096,965.

(51) Int. Cl.
*A61H 1/02* (2006.01)
*A61F 5/01* (2006.01)

(52) U.S. Cl.
CPC ........... *B25J 9/0006* (2013.01); *A61F 5/0102* (2013.01); *A61H 2003/001* (2013.01); *A61H 2201/1207* (2013.01); *A61H 2201/163* (2013.01); *A61H 2201/164* (2013.01); *A61H 2201/165* (2013.01); *A61H 2201/1621* (2013.01); *A61H 2201/1642* (2013.01); *A61H 2201/1676* (2013.01); *A61H 2201/5007* (2013.01); *A61H 2201/5058* (2013.01); *A61H 2201/5061* (2013.01); *A61H 2201/5097* (2013.01)

(56) References Cited

U.S. PATENT DOCUMENTS

| | | | |
|---|---|---|---|
| 7,153,242 B2 | 12/2006 | Goffer | |
| 7,410,471 B1 | 8/2008 | Campbell et al. | |
| 7,860,562 B2* | 12/2010 | Endo | A61B 5/04888 600/546 |
| 7,883,483 B2* | 2/2011 | Ido | A61H 3/00 482/66 |
| 7,998,096 B1* | 8/2011 | Skoog | A61H 3/00 601/35 |
| 8,096,965 B2 | 1/2012 | Goffer et al. | |
| 8,251,930 B2* | 8/2012 | Ido | A61H 1/0237 601/23 |
| 2003/0093021 A1 | 5/2003 | Goffer | |
| 2003/0120183 A1 | 6/2003 | Simmons | |
| 2005/0177080 A1* | 8/2005 | Yasuhara | A61B 5/112 602/16 |
| 2005/0251079 A1* | 11/2005 | Carvey | A61F 5/0102 602/26 |
| 2006/0046910 A1* | 3/2006 | Rastegar | A61H 3/00 482/91 |
| 2006/0206167 A1* | 9/2006 | Flaherty | A61H 1/0255 607/48 |
| 2006/0206214 A1 | 9/2006 | Clausen et al. | |
| 2007/0056592 A1* | 3/2007 | Angold | A61H 3/00 128/845 |
| 2007/0123997 A1 | 5/2007 | Herr et al. | |
| 2008/0039756 A1* | 2/2008 | Thorsteinsson | A61B 5/1038 602/23 |
| 2008/0154165 A1* | 6/2008 | Ashihara | A61F 5/0102 602/23 |
| 2008/0234608 A1* | 9/2008 | Sankai | A61B 5/04888 601/5 |
| 2010/0121232 A1* | 5/2010 | Sankai | A61H 3/008 601/23 |
| 2012/0101415 A1 | 4/2012 | Goffer et al. | |

FOREIGN PATENT DOCUMENTS

| | | |
|---|---|---|
| WO | WO 2006/078871 A2 | 7/2006 |
| WO | WO 2010/044087 A2 | 4/2010 |

OTHER PUBLICATIONS

European Search Report of European Application No. EP 09 82 0341 dated Jun. 10, 2015.
Boyd "Bionic suit offers wearers super-strength" new Scientist Print Edition, Issue 2494, Apr. 9, 2005.
Office Action dated Feb. 2, 2016 by Canadian Intellectual Property Office for Application No. 2,740,438, filed Oct. 13, 2009.
Examination Search Report dated Feb. 2, 2016 by Canadian Intellectual Property Office for Application No. 2,740,438, filed Oct. 13, 2009.

* cited by examiner

LOCOMOTION ASSISTING DEVICE AND METHOD

CROSS-REFERENCE TO RELATED APPLICATIONS

This application is a divisional application of U.S. patent application Ser. No. 13/735,160 filed Jan. 7, 2013, which is a divisional application of U.S. patent application Ser. No. 13/350,852, filed Jan. 16, 2012 and issued as U.S. Pat. No. 8,348,875, which is a divisional application of U.S. patent application Ser. No. 12/250,155, filed Oct. 13, 2008 and issued as U.S. Pat. No. 8,096,965, all of which are hereby incorporated by reference.

FIELD OF THE INVENTION

The present invention relates to control of a device for assistance with locomotion. More particularly, the present invention relates to a locomotion assisting device and method.

BACKGROUND OF THE INVENTION

Motorized locomotion assisting exoskeleton devices have been proposed for assisting people with disabilities to walk or to perform other tasks. In addition to enabling the performance of the tasks, enabling a person to walk may also impart therapeutic benefits. However, a major difficulty with such devices has been the lack of ability to control such devices in an effective, safe, and intuitive manner.

U.S. Pat. No. 7,153,242 (Goffer) describes an apparatus for enabling a person with handicapped lower limbs to walk. The apparatus attaches to parts of the lower portion of the person's body, possibly up to the torso, and includes motorized means of propelling the parts of the body to which it is attached. The apparatus includes sensors for measuring the angles of the joints, and a sensor for measuring the tilt angles of the upper body. The person using the apparatus selects a mode of operation, such as a gait. Initiation and maintaining of a gait is indicated by the tilt of the upper body of the person using the apparatus. For example, leaning forward triggers a forward step, and swinging the upper body from an upright position to a forward bend maintains a walking gait sequence wherein the apparatus performs the required sequence of movements of the lower limbs, including lifting, extending, bending, and lowering. However, such control by means of measuring the tilt of the upper body may be insufficient. For example, tilting the upper body does not enable the user of the apparatus to indicate with which leg to initiate the gait. Thus, user control is limited. In addition, such an apparatus does not provide control feedback for monitoring the phases and progress of the gait, and cannot alert the user to hazardous situations such as a forbidden arrangement of the feet.

Another powered exoskeleton, called a "hybrid assistive limb" or "HAL," is described by Boyd in "Bionic suit offers wearers super-strength" (New Scientist, issue 2494, 9 Apr. 2005). Two control methods are described. In the first method described, sensors on the skin detect electric nerve signals from the brain to the leg muscles that indicate intention to move a leg. The device guides movement of the legs in accordance with the user's intentions. In the second described method, sensors detect when the user has started to move. The device then activates itself automatically to augment the power of user's muscles. Neither control method may be used by a paraplegic user whose nerves do not transmit signals from the brain to the legs.

It is an object of the present invention to provide an apparatus and method for controlling a locomotion assisting exoskeleton device in an intuitive and natural manner by a paraplegic or other user, and for providing feedback with regard to performance.

It is a further object of the present invention to provide an apparatus and method for enhancing the safety of a locomotion assisting exoskeleton device.

Other aims and advantages of the present invention will become apparent after reading the present invention and reviewing the accompanying drawings.

SUMMARY OF THE INVENTION

There is thus provided, in accordance with some embodiments of the present invention, an exoskeleton bracing system. The system comprises: a trunk support for affixing to the trunk of a disabled person, leg braces for connecting to the legs of the person with each leg brace including limb segment braces, motorized joints adapted to provide relative angular movement between the limb segment braces of the leg braces and between the leg braces and the trunk support, one or more ground force sensors designed to sense ground force exerted on each of the leg braces, and a controller for receiving sensed signals from the ground force sensors. An algorithm identifies a stance from the sensed signals and, based on the identified stance, actuates the motorized joints to perform an action relating to a mode of locomotion selected from a set of predefined actions corresponding to the identified stance Furthermore, in accordance with some embodiments of the present invention, the algorithm includes selecting an action comprising actuating the motorized jointed limb braces of one leg, when the sensed signals are indicative of the person leaning on the opposite leg.

Furthermore, in accordance with some embodiments of the present invention, the algorithm includes selecting an action comprising actuating the motorized jointed limb braces of one leg, when the sensed signals are indicative of the person leaning on the same leg.

Furthermore, in accordance with some embodiments of the present invention, the algorithm includes selecting an action comprising ending a currently performed action when the sensed signals are indicative of substantially equally loading both legs.

Furthermore, in accordance with some embodiments of the present invention, the algorithm includes selecting an action comprising ending a currently performed action when the sensed signals are indicative of the person leaning on a trailing leg.

Furthermore, in accordance with some embodiments of the present invention, the system comprises an alerting device, the algorithm includes selecting an action comprising generating an alert from the alerting device.

Furthermore, in accordance with some embodiments of the present invention, the system comprises an alerting device, the action of generating an alert from the alerting device is performed when the sensed signals are indicative of the person falling Furthermore, in accordance with some embodiments of the present invention, the system comprises an alerting device, the action of generating an alert from the alerting device is performed to indicate that the user is to change the stance.

Furthermore, in accordance with some embodiments of the present invention, the algorithm includes selecting an action comprising continuing a currently performed action when the sensed signals are indicative of increasing ground force.

Furthermore, in accordance with some embodiments of the present invention, the algorithm includes selecting an action comprising continuing a currently performed action when the sensed signals are indicative of decreasing ground force.

Furthermore, in accordance with some embodiments of the present invention, the system comprises a mode selector for selecting the mode of locomotion from a set of predefined locomotion modes.

Furthermore, in accordance with some embodiments of the present invention, the mode selector is adapted to communicate with the controller via wireless communication.

Furthermore, in accordance with some embodiments of the present invention, the mode selector includes a strap for strapping on a wrist.

Furthermore, in accordance with some embodiments of the present invention, the mode selector includes controls for selecting modes of locomotion from a group of locomotion modes consisting of: walking, standing from a sitting position, sitting from a standing position, climbing a stair and descending a stair.

Furthermore, in accordance with some embodiments of the present invention, the system comprises a tilt sensor to sense tilt of the trunk of the person with respect to the vertical and to communicate with the controller.

Furthermore, in accordance with some embodiments of the present invention, the identified stance is determined from the signals received from said one or more ground force sensors and a signal from the tilt sensor.

Furthermore, in accordance with some embodiments of the present invention, the action is selected from a group of actions consisting of: initiating a gait, maintaining a gait, halting a gait, climbing a stair, and descending a stair.

Furthermore, in accordance with some embodiments of the present invention, the action comprises enabling continuation of the mode of locomotion.

Furthermore, in accordance with some embodiments of the present invention, there is provided a method of controlling an exoskeleton bracing system that includes a trunk support for affixing to the trunk of a disabled person, leg braces for connecting to the legs of the person, each leg brace including limb segment braces, motorized joints adapted to provide relative angular movement between the limb segment braces of the leg braces and between the leg braces and the trunk support, and a controller. The method comprises: providing one or more ground force sensors designed to sense ground force exerted on each of the leg braces, receiving sensed signals from the ground force sensors, identifying a stance from the sensed signals, and actuating the motorized joints based on the identified stance to perform an action relating to a mode of locomotion selected from a set of predefined actions that relates to the identified stance.

Furthermore, in accordance with some embodiments of the present invention, the step of identifying the stance comprises identifying a stance determined by the person.

Furthermore, in accordance with some embodiments of the present invention, the identified stance comprises leaning on one leg and the selected action comprises actuating the motorized jointed limb braces of the opposite leg.

Furthermore, in accordance with some embodiments of the present invention, the identified stance comprises leaning on one leg and the selected action comprises actuating the motorized jointed limb braces of the same leg.

Furthermore, in accordance with some embodiments of the present invention, the identified stance comprises standing on both legs and the selected action comprises ending a currently performed action.

Furthermore, in accordance with some embodiments of the present invention, the identified stance comprises leaning on a trailing leg and the selected action comprises ending a currently performed action.

Furthermore, in accordance with some embodiments of the present invention, the selected action comprises generating an alert.

Furthermore, in accordance with some embodiments of the present invention, the system comprises an alerting device, the action of generating an alert from the alerting device is performed when the sensed signals are indicative of the person falling Furthermore, in accordance with some embodiments of the present invention, the system comprises an alerting device, the action of generating an alert from the alerting device is performed to indicate that the user is to change the stance.

Furthermore, in accordance with some embodiments of the present invention, the identified stance comprises falling and the selected action comprises generating an alert.

Furthermore, in accordance with some embodiments of the present invention, the method comprises detecting increasing ground force to verify the selected action.

Furthermore, in accordance with some embodiments of the present invention, the method comprises detecting decreasing ground force to verify the selected action.

Furthermore, in accordance with some embodiments of the present invention, the method comprises providing at least one tilt sensor, sensing the tilt of a body part of the person, and using the sensed tilt in the step of actuating the motorized joints.

Furthermore, in accordance with some embodiments of the present invention, the action is selected from a group consisting of: initiating a gait, maintaining a gait, halting a gait, climbing a stair, and descending a stair.

Furthermore, in accordance with some embodiments of the present invention, the mode of locomotion is selected from a group of locomotion modes consisting of: walking, standing from a sitting position, sitting from a standing position, climbing a stair and descending a stair.

Furthermore, in accordance with some embodiments of the present invention, the action comprises enabling continuation of the mode of locomotion.

BRIEF DESCRIPTION OF THE DRAWINGS

In order to better understand the present invention, and appreciate its practical applications, the following Figures are provided and referenced hereafter. It should be noted that the Figures are given as examples only and in no way limit the scope of the invention. Like components are denoted by like reference numerals.

FIG. 1A1 shows a locomotion assisting exoskeleton device in accordance with embodiments of the present invention.

FIG. 1A2 shows a tilt sensor for use in a locomotion assisting exoskeleton device in accordance with embodiments of the present invention.

DETAILED DESCRIPTION OF EMBODIMENTS

Figure 1B:
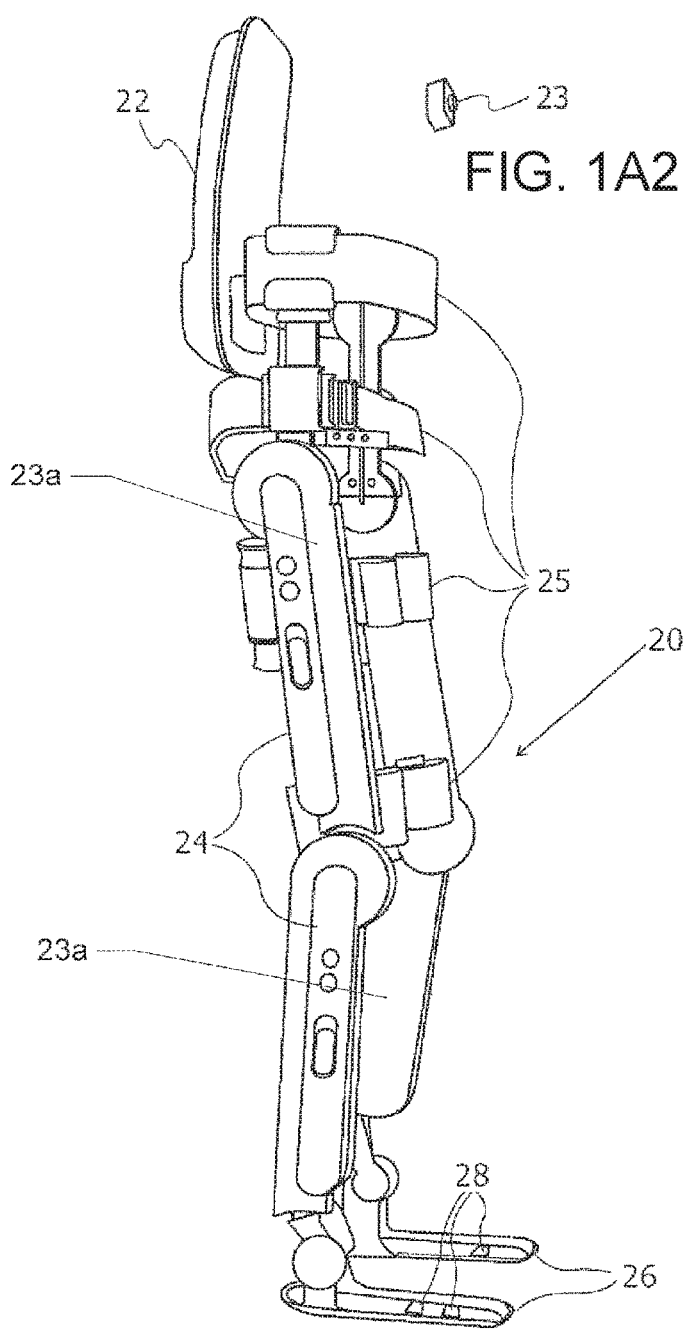
FIG. 1B shows a control panel unit associated with the locomotion assisting exoskeleton device shown in FIG. 1A.
Figure 1B:
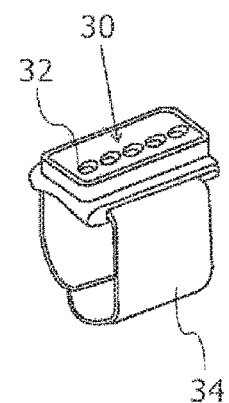

In accordance with embodiments of the present invention, an apparatus and method are provided to enable effective control and monitoring of a motorized locomotion assisting exoskeleton device by means of ground force measurement. By "ground force measurement" is meant a local measurement of the force that is exerted by an area of a supporting surface that counters the force exerted on that area of the surface by the user. The supporting surface may be a floor, or ground, below the user, or any other horizontal or non-horizontal surface that supports the weight of, or otherwise supports or stabilizes the user, or counters a force exerted by the user or the locomotion assisting exoskeleton device. The ground force may be a force applied directly by the supporting surface on a component of the locomotion assisting exoskeleton device, or may be transmitted via a body or object that is between the supporting surface and the component.

The locomotion assisting exoskeleton device includes braces and supports that may be strapped on, or otherwise attached or affixed to, the trunk and sections of limbs and body parts in the lower portion of the body of a user. The various braces and supports are connected to one another by means of joints that enable relative movement between the braces and supports. The locomotion assisting exoskeleton device may include motorized actuation assemblies or joints for moving parts of the user's body, such as for bending joints in order to propel various limbs of the user's body. The locomotion assisting exoskeleton device may also include sensors for measuring relative situation of various components of the device, and thus of the body parts to which they are attached. Such sensors may measure, for example, the angle between the brace sections on either side of a joint.

In addition, the locomotion assisting exoskeleton device may include one or more sensors that sense or measure tilt. For example, such a sensor affixed to the upper portion of the user's body may measure the tilt of that portion of the body.

The user of the locomotion assisting exoskeleton device is provided with a set of controls that communicate with the locomotion assisting exoskeleton device. By means of the controls, the user may select a locomotion mode for the device. Available modes may include walking, climbing a stair, descending a stair, sitting, and standing from a sitting position.

In accordance with embodiments of the present invention, the locomotion assisting exoskeleton device includes a foot brace that is positioned under a foot of the user. The foot brace supports the foot of the user, and applies force to the user's foot that counters the force of the weight of the user on the foot brace. The foot brace is provided with one or more ground force sensors. Ground force sensors are known in the art. For example, a ground force sensor may be based on a force sensitive resistor, such as a piezoresistive force sensor. A ground force sensor generates a signal that indicates the force that is applied to it. The amount of force applied to the ground force sensor depends on the posture or stance of the user, or on the activity of the user.

When a locomotion mode is selected, the locomotion assisting exoskeleton device awaits an instruction before initiating the appropriate motion sequence. In accordance with embodiments of the present invention, instructions are provided in accordance with signals generated by the ground force sensors of a foot brace. By shifting the weight of the user's body, perhaps with the aid of crutches, the user may increase or decrease the force applied to one or more of the ground force sensors.

For example, if a walking gait mode was selected and the user wishes to begin walking with the right foot, the user slightly leans on the left foot (perhaps with concurrent use of crutches). A ground force sensor on the right foot brace may then generate a signal indicating decreased force and a force sensor of the left foot brace may indicate increased force. The locomotion assisting exoskeleton device then initiates the walking gait by lifting and extending the right foot brace. The locomotion assisting exoskeleton device continues to monitor the signals generated by the ground force sensors. Thus, the user retains control over the gait. By leaning or otherwise controlling the force on the ground force sensors in an expected manner, the user continues to enable the gait. If, however, the weight of the user shifts in a manner inconsistent with the current phase of the gait, the locomotion assisting exoskeleton device may alert the user or halt the gait or converge to a stance until further instructions are received.

FIG. 1A shows a motorized locomotion assisting exoskeleton device that is controlled in accordance with embodiments of the present invention. Locomotion assisting exoskeleton device 20 is powered and controlled by controller pack 22. Controller pack 22 incorporates a controller in the form of a programmable processor, and a battery or other power supply (shown schematically in FIG. 1C). Controller pack 22 is generally worn on the back of a person using locomotion assisting exoskeleton device 20. Alternatively, the various components of controller pack 22 may be attached to or incorporated in various components of exoskeleton device 20. For example, components of controller pack 22 may be incorporated into braces 24.

Controller pack 22 may communicate with a tilt sensor 23 that is fixed to a location on the upper portion of the user's body. For example, tilt sensor 23 may be worn on a shoulder strap that holds controller pack 22 to the user's torso, and thus senses the degree of tilt of the torso. The tilt sensors may include accelerometers, gyroscopes, or any other sensors capable of being incorporated in a locomotion assisting exoskeleton device and designed to sense tilt. The tilt sensor generates a signal that indicates whether the user's upper portion of the body is leaning or is upright with respect to the vertical Braces 23 are affixed by means of straps 25 to segments of the user's lower limbs and to the pelvis, torso, or other parts of the user's body. Braces 23 incorporate motorized actuation assemblies 24. Each actuation assembly 24 includes a motorized actuator (not shown) that, in response to commands transmitted by controller pack 22, causes a joint that connects between individual braces 23 to bend or extend. Bending or extending a joint may propel or move a limb to which an adjoining brace is attached. When the lower limbs of the user are affixed to braces 23, each of the user's feet is placed on a foot brace 26. Foot brace 26 may be movable by means of a separate motorized actuation assembly (not shown) to lift, guide, and lower a foot of the user. Alternatively, foot brace 26 may include a coil, spring, or other elastic anti-drop mechanism associated with ankle joint 27. The anti-drop mechanism associated with ankle joint 27 holds foot brace 26 substantially horizontal when foot brace 26 is raised above, and is not supported by, a supporting surface.

FIG. 1B shows a control panel unit associated with the motorized locomotion assisting exoskeleton device shown in FIG. 1A. Control panel unit 30 communicates with controller pack 22 via a wireless or other communications channel. Typically, control panel unit 30 is strapped to the user's wrist by means of straps 34. Control panel unit 30 includes one or more touch-sensitive buttons or keys 32. The touch-sensitive buttons 32 may serve as a mode selector to select a mode of locomotion, to verify a command, or to communicate other instructions to controller pack 22.

One or more ground force sensors 28 are mounted on each foot brace 26. Each of ground force sensors 28 is capable of generating a signal that indicates the force applied to that sensor. Signals generated by ground force sensors 28 are transmitted to controller pack 22. Controller pack 22 receives signals transmitted by control panel unit 30 and by ground force sensors 28. On the basis of the received signals and in accordance with programmed instructions, controller pack 22 transmits instructions to actuation assemblies 24. The instructions transmitted to actuation assemblies 24 may cause one or more of braces 23 to move, propelling any limbs attached to the units.

By activating buttons 32 and by adjusting the force on ground force sensors 28, a person may control locomotion assisting exoskeleton device 20 to assist in performing a desired task. Examples of controlling a locomotion assisting exoskeleton device in accordance with embodiments of the present invention are described below.

Figure 1C:
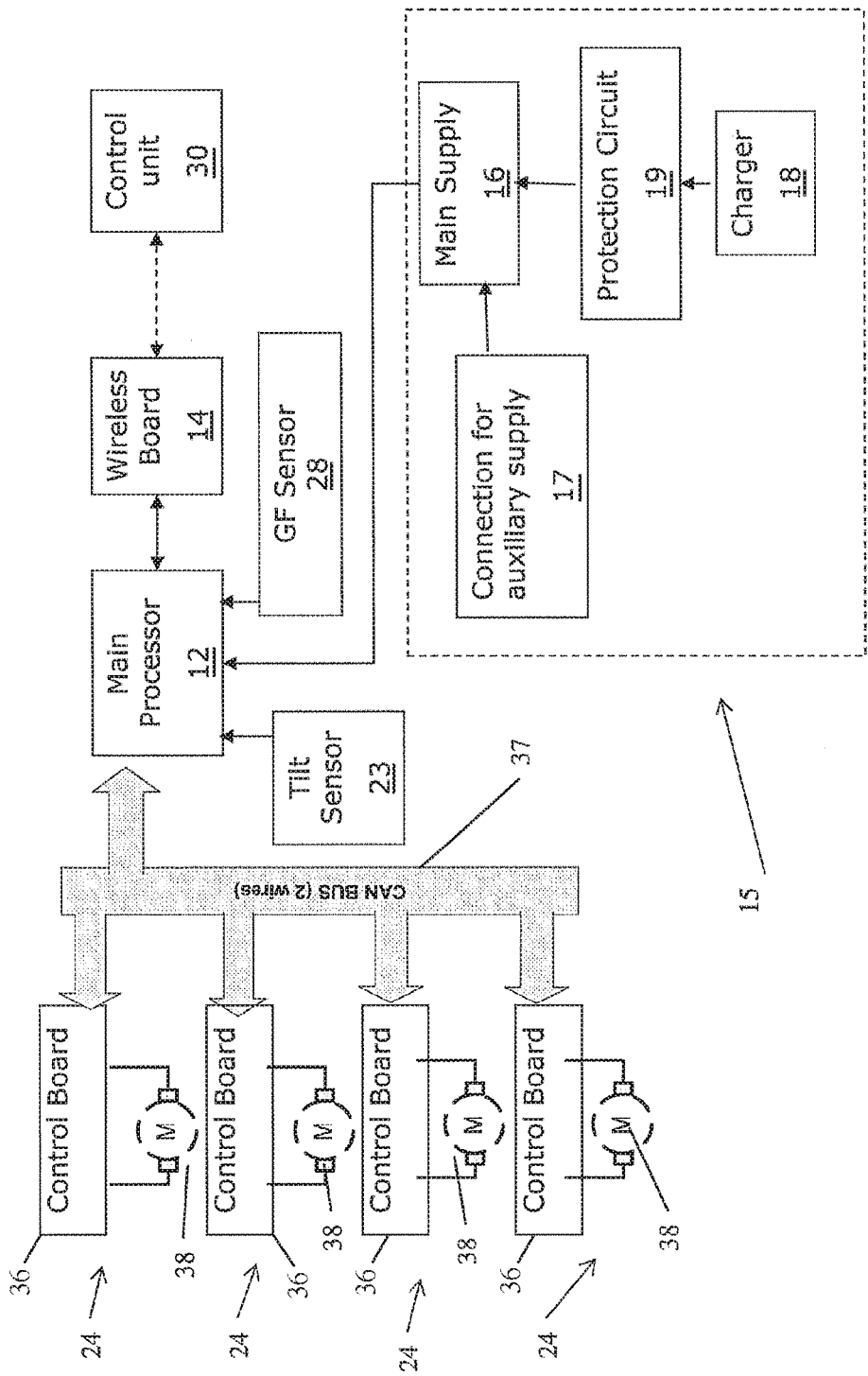
FIG. 1C is a block diagram of the locomotion assisting exoskeleton device shown in FIG. 1A and FIG. 1B.

FIG. 1C is a block diagram of the locomotion assisting exoskeleton device shown in FIG. 1A and FIG. 1B. Power supply 15 is located in controller pack 22. Main supply 16 provides power to main processor 12, actuation assemblies 24, and motors 38. Main supply 16 may include a rechargeable battery that may be charged by means of charger unit 18 that may be connected to main supply 16 through protection circuit 19. When necessary, an appropriate alternative external power source, such as an auxiliary battery, may be connected to auxiliary connection 17.

Main processor 12 may receive signals from tilt sensor 23 and ground force sensors 28. Main processor 12 may communicate with control unit 30 over a wireless connection through wireless communications board 14. Main processor 12 communicates with actuation assemblies 24 via communications channels, such as controller-area network (CAN) bus 37. Each actuation assembly 24 includes a control board 36. Each control board 36 controls a motor 38 that determines the motion of actuation assembly 24, and thus of a brace or joint to which actuation assembly 24 may be attached.

In general, a user of locomotion assisting exoskeleton device 20 selects a mode of operation. Modes of operation may include selection of a task to be carried out. Examples of such tasks may include walking with a particular gait, sitting, standing from a sitting position, climbing stairs, and descending stairs.

The locomotion assisting exoskeleton device may include one or more alerting devices for alerting the user of situations demanding the user's attention. Such alerting devices may generate audible, visible, or tactile alert signals. The alerting devices may be incorporated into one or more components of the locomotion assisting exoskeleton device. Situations requiring user attention may include contradictory or unexpected movements or foot loading, falling, and points during the execution of a procedure where user verification is required for safety purposes.

Depending on the details of the control algorithm for the motorized locomotion assisting exoskeleton device, the ground force sensor values used in controlling the locomotion assisting exoskeleton device may represent a signal generated by a single sensor, or may be a representative value of the signals based on processing the outputs generated by part or all of an array of sensors associated with a single foot brace. Alternatively, the value used may represent a pattern or map of forces applied to the sensors of one or both foot braces.

For the sake of simplicity in the discussion below, the values of forces measured by the ground force sensors, or foot loadings, may be classified into one of four loading categories. The ranges of sensor signals to be included within each loading category may vary from user to user, or from one mode of operation to another. The loading categories may also be defined relative to one another. The category representing the range of the smallest forces may be labeled "foot off" (FO), and is associated with a foot brace that is not touching the ground. The category representing the next larger range of forces may be labeled "foot touching" (FT), associated with a foot brace that is touching the ground, but with minimal loading. The category representing the next larger range of forces labeled "foot lightly loaded" (FLL), may represent light loading on a foot brace, associated with a situation where the user is standing on both feet, and load of the weight of the body is shared with the other foot brace. Finally, a category representing the range of greatest forces may be labeled "foot heavily loaded" (FHL). FHL is associated with a user leaning on one foot brace, with that foot brace supporting most of the weight of the user's body.

In addition to the signal output of ground force sensors, control of the locomotion assisting exoskeleton device may utilize a measurement of the tilt of the upper part of the user's body. The tilt measurement may be used to check whether the tilt of the user's body is consistent with the current phase of an activity. In addition, depending on the control algorithm of the locomotion assisting exoskeleton device, the user may use body tilt, in addition to applying force to the ground force sensors, to control the locomotion assisting exoskeleton device.

Loading on a particular foot, the right or the left foot is indicated in the discussion below by preceding the abbreviation for a loading category with the letter R or L, respectively. For example, the right foot lightly loaded may be designated RFLL. The left foot touching may be designated LFT.

Various combinations of loading on the right and left legs may indicate various stances. A stance is to be understood as including any posture of the body, such as, for example, standing, sitting, or a phase of a walking gait, including an unstable or falling posture, and not only a stable standing posture. For example, a loading combination RFLL and LFLL may indicate that the user is standing straight or otherwise placing approximately equal loading on both legs. A combination of RFHL with lighter loading on the left leg, LFLL, LFT, or LFO, may be indicate that the user is leaning on the right leg. Conversely, a combination of LFHL with RFLL, RFT, or RFO may indicate leaning on the left leg. Leaning on a leg is understood to include standing on one leg with the other leg being held above the ground. Any combination of FLL, FT, or FO loading on one leg, combined with FT or FO loading on the other leg, may indicate falling. Falling may also be indicated by a tilt sensor. During falling, the tilt sensor may indicate that the upper body is tilted at an angle indicative of falling, or may indicate acceleration indicative of falling.

In the diagrams discussed below, the left leg is designated LG, the right leg is designated RG, and ground force sensors are designated GF. In the examples of the control methods described below, the user may coordinate the action of the locomotion assisting exoskeleton device with the use of crutches. However, the role of the crutches is not indicated in the Figures.

Figure 2A:
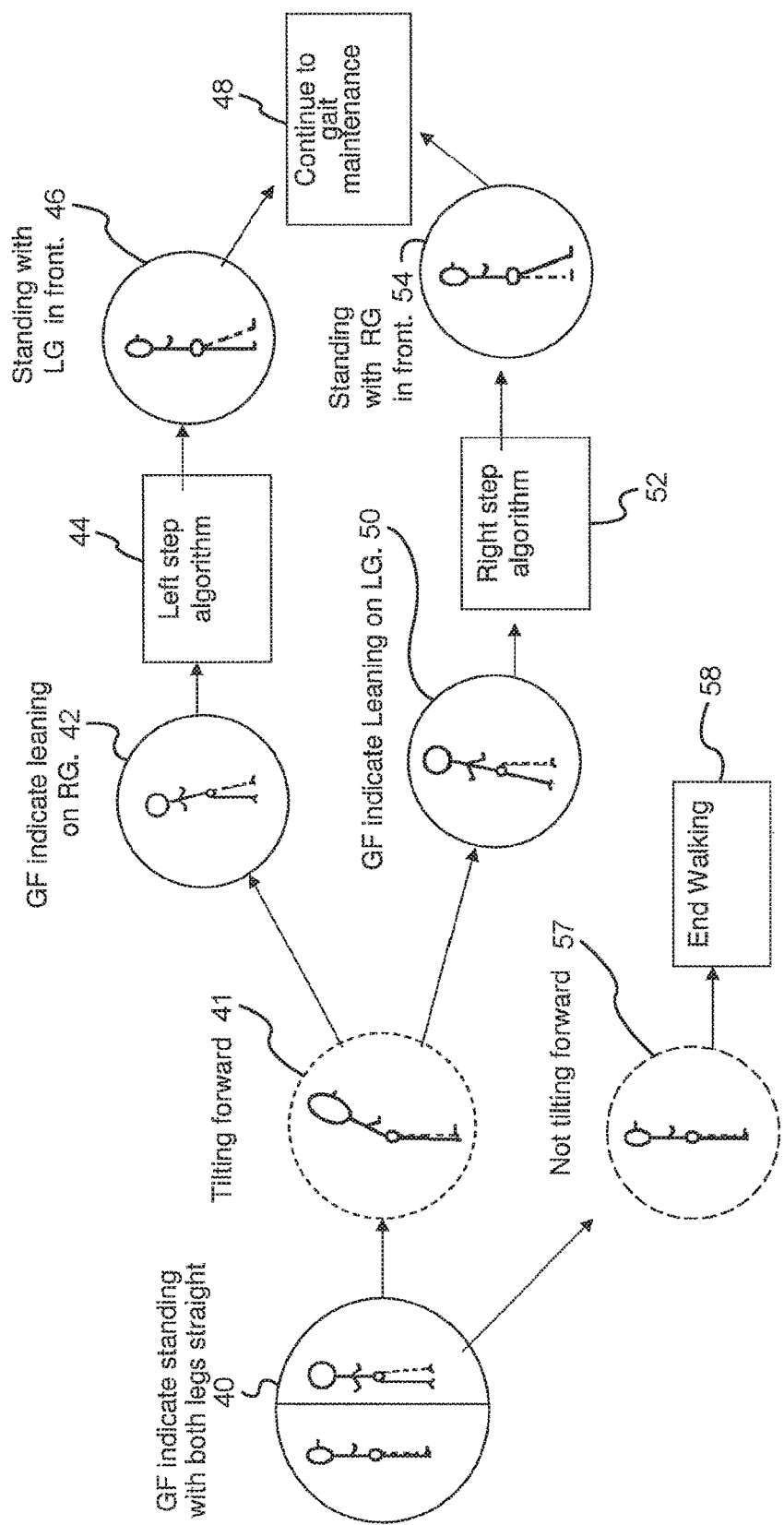
FIG. 2A is a diagram of a control process for initiating a step from a standing position, in accordance with embodiments of the present invention.
Figure 2B:
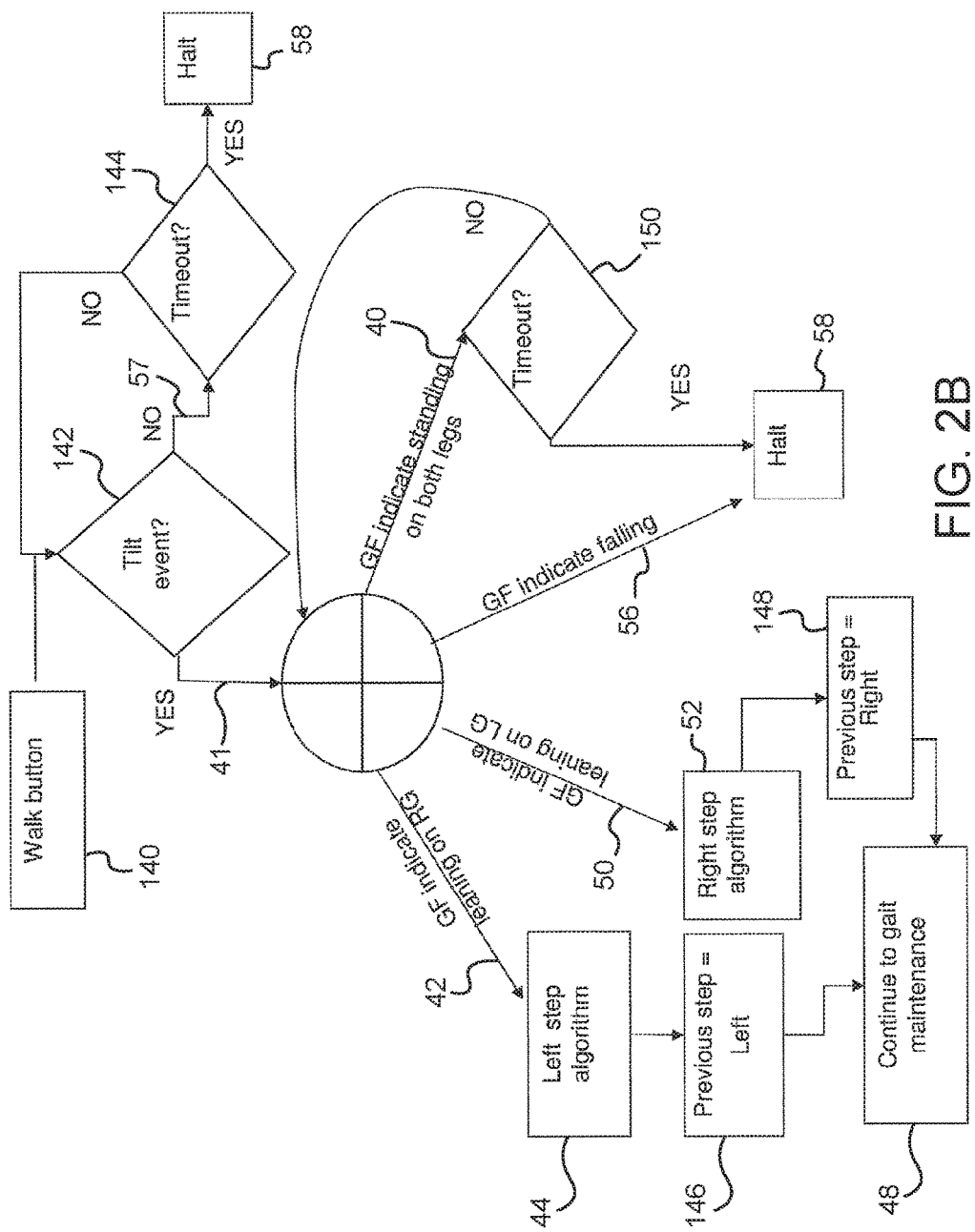
FIG. 2B is a flow chart of the control process illustrated in FIG. 2A.

FIG. 2A is a diagram of the control process for initiating a step from a standing position, in accordance with embodiments of the present invention. FIG. 2B is a flow chart of a control method for the process illustrated in FIG. 2A. By means of the controls on the control panel unit of the exoskeleton skeleton device, the user indicates the intention to initiate a walking gait (step 140). The control system of the locomotion assisting exoskeleton device then checks whether tilt sensors indicate that the user is leaning forward (step 142). If not (step 57), the system checks whether a predetermined time has elapsed since step 140 (step 144). If the time has elapsed, the process of initiating a walking gait times out and is halted (step 58). If not, the system continues to wait for an appropriate signal from the tilt sensors (return to step 142).

The user initiates the walking gait by leaning forward (step 41). The user may be initially standing with weight distributed approximately equally between both legs (as in step 40, RFLL and LFLL loading). If no change in loading is detected by the ground force sensors within a predetermined period of time (step 150), the process of initiating a walking gait times out and is halted (step 58). The user may lean on the right leg (RFHL loading, step 42) to instruct the locomotion assisting exoskeleton device to begin a walking gait, stepping with the left leg first. Leaning on the right leg is a relatively intuitive way of indicating that the user wishes to start walking by stepping with the left leg. When the control system detects leaning on the right leg, the system executes an algorithm (step 44) causing the locomotion assisting exoskeleton device to extend the left leg. The user is then standing with left leg extended (step 46). The system records that a walking step was made with the left leg (step 146) and the gait maintenance process (described below) begins (step 48). If the user prefers to start the gait with the right leg, the user leans on the left leg (LFHL loading, step 50). This initiates a walking step with the right leg (step 52 and step 54) that is recorded by the system (step 148). During the process of initiating a gait, the locomotion assisting exoskeleton device continues to monitor the ground force sensors. Should the ground force sensors indicate falling (step 56, FLL, FT, or FO loading on one leg combined with a FT or FO loading on the other), or a tilt sensor indicate falling, the walking gait initiation procedure is halted (step 58).

Figure 3:
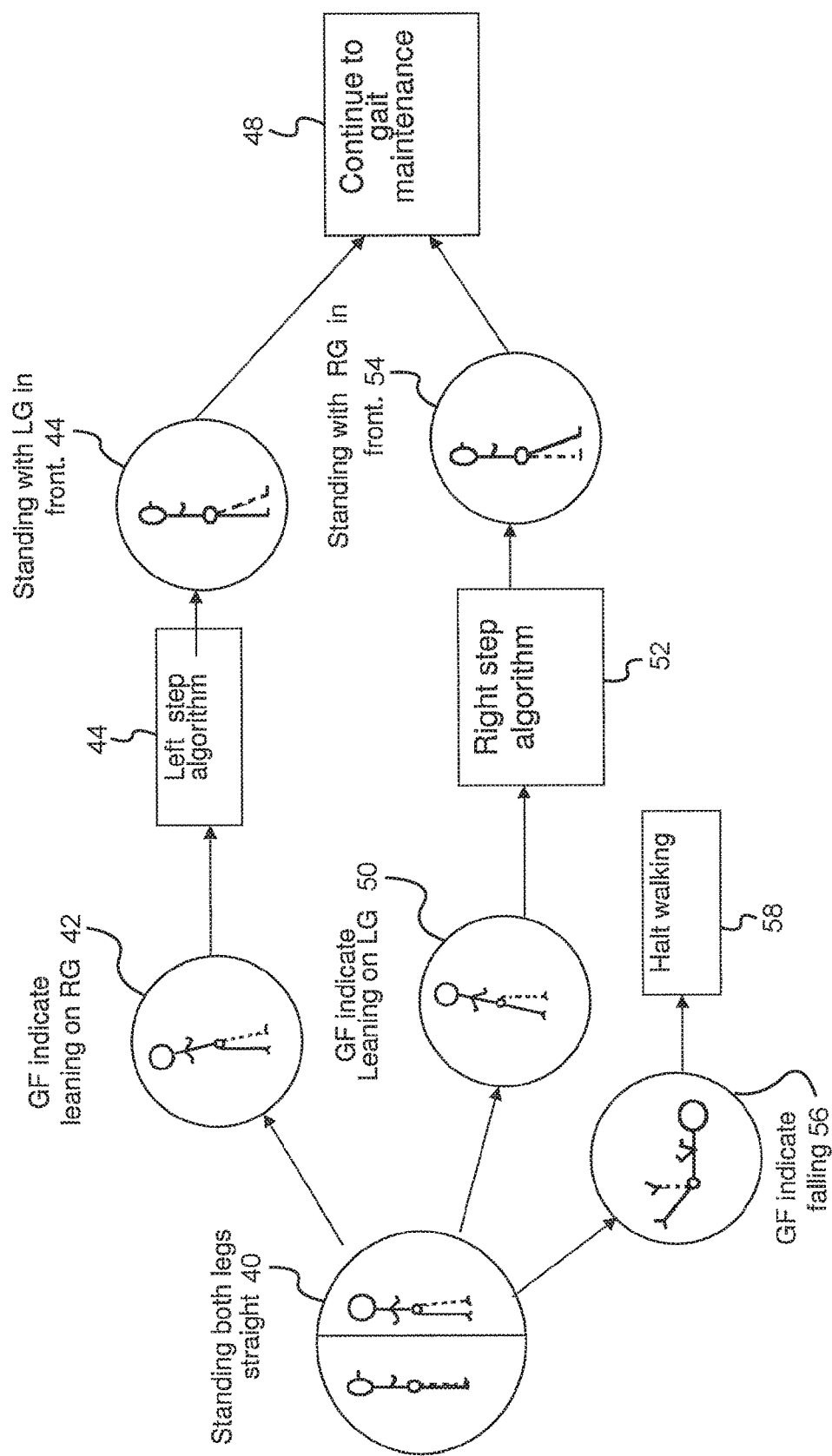
FIG. 3 is a diagram of a control process for initiating a step from a standing position using only ground force sensors, in accordance with embodiments of the present invention.

Alternatively, initiating a gait by the locomotion assisting exoskeleton device may be controlled by means of activating the ground force sensors alone, without waiting for a signal from a tilt sensor. FIG. 3 is a diagram of control for initiating a step from a standing position using only ground force sensors, in accordance with embodiments of the present invention. Leaning on either leg initiates the gait initiation process. If the ground force sensors do not indicate that the user has leaned on either leg within a predetermined period of time, the gait initiation process times out and is halted.

Figure 4A:
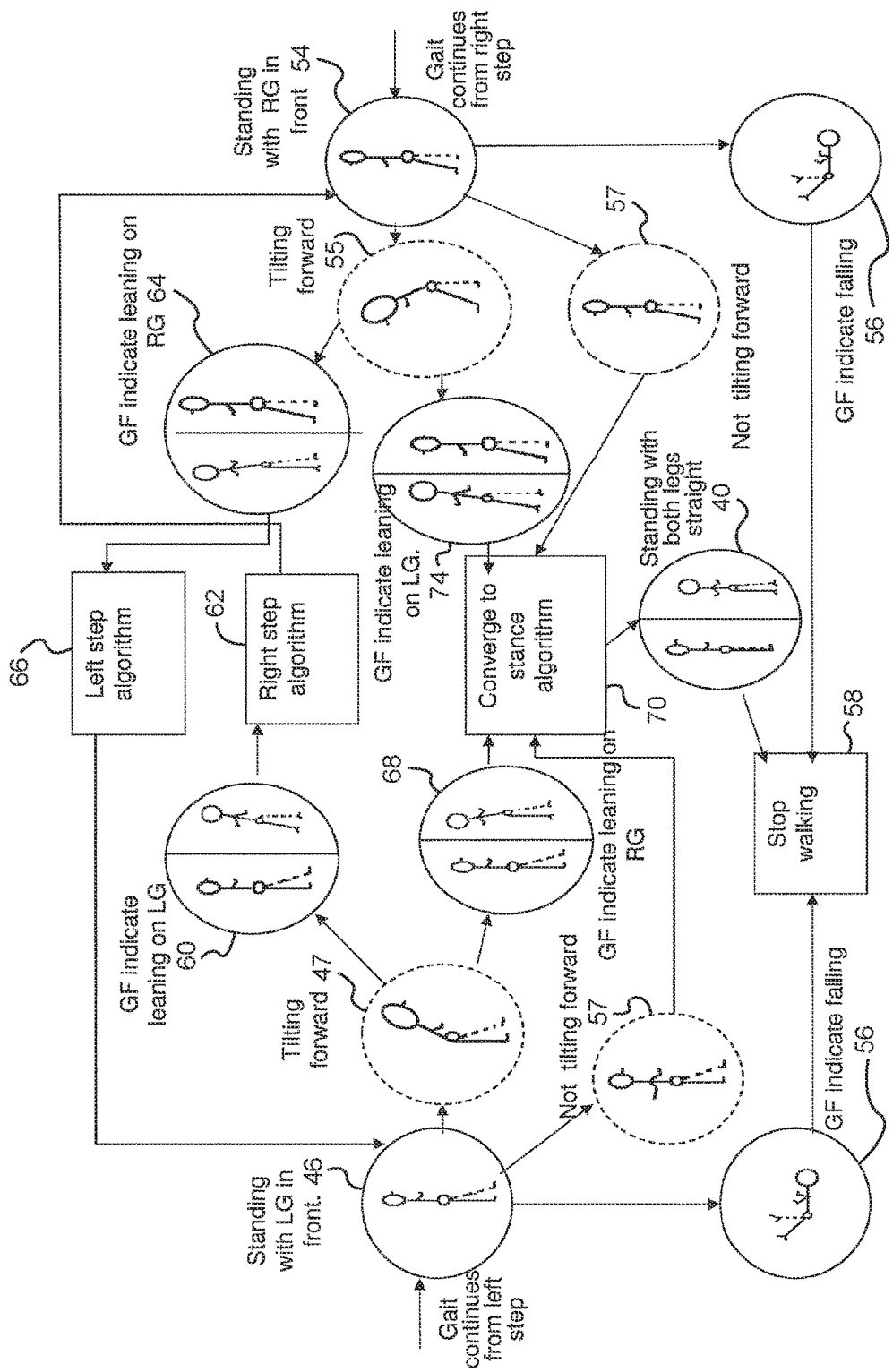
FIG. 4A is a diagram of a control process for maintaining a gait, in accordance with embodiments of the present invention.
Figure 4B:
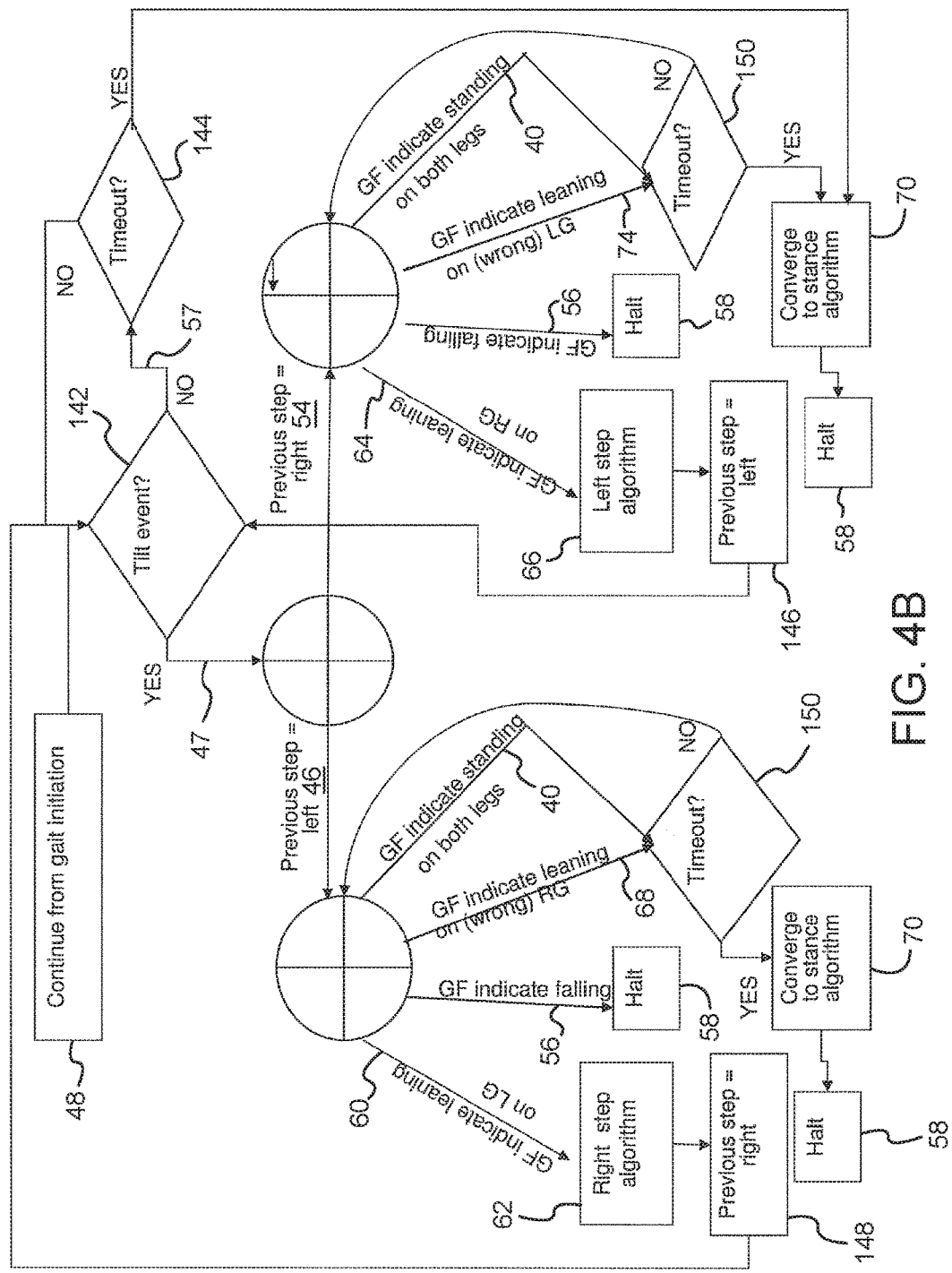
FIG. 4B is a flow chart of the control process illustrated in FIG. 4A.

FIG. 4A is a diagram of the control process for maintaining a gait, in accordance with embodiments of the present invention. FIG. 4B is a flow chart of a control method for the process illustrated in FIG. 4A. Before initiating another walking step of the gait, the system checks if the tilt sensors indicate that the user is leaning forward. If not (step 57), and a predetermined time period has elapsed (step 144), the gait maintenance process times out. When the process times out, an algorithm is executed (step 70) to bring both legs to a standing position (step 40) and the process is halted (step 58).

The user indicates the intention to continue the walking gate by continuing to lean forward (step 47). If the previous step of the gait was executed with the left leg, the user may be standing in the position of step 46, with left leg extended forward. The user leans on the extended left leg (step 60) to instruct the locomotion assisting exoskeleton device to continue the walking gait by extending the right leg (step 62). The system records that the last step of the gait was executed with the right leg. The user is now in the position of step 54, with right leg extended. On the other hand, while standing in the position of step 46, the user may lean on the trailing right leg (step 68) or on both legs with about equal force. Continuing to lean on the trailing right leg or on both legs for a predetermined time interval (step 150) instructs the locomotion assisting exoskeleton device to halt the walking gait. The system executes an algorithm (step 70) to bring the user's legs together to a standing stance, to the position of step 40. The walking process is then halted (step 58).

If the previous step of the gait was executed with the right leg so that the user stands with right leg extended (step 54), the user may lean on the extended right leg to instruct the locomotion assisting exoskeleton device to continue a forward gait by extending the left leg (step 64). The locomotion assisting exoskeleton device then executes a step of the gait with the left leg forward (step 66) so that the user is standing with the left leg extended (step 46). The system records that a step was executed with the left leg (step 146). On the other hand, while still standing in the position of step 54, leaning on the trailing left leg (step 74) or about equally on both legs (step 40) for a predetermined time interval (step 150)

instructs the locomotion assisting exoskeleton device to bring the user to a standing position (step 70 and step 40) and to stop the gait maintenance process (step 58).

Figure 5:
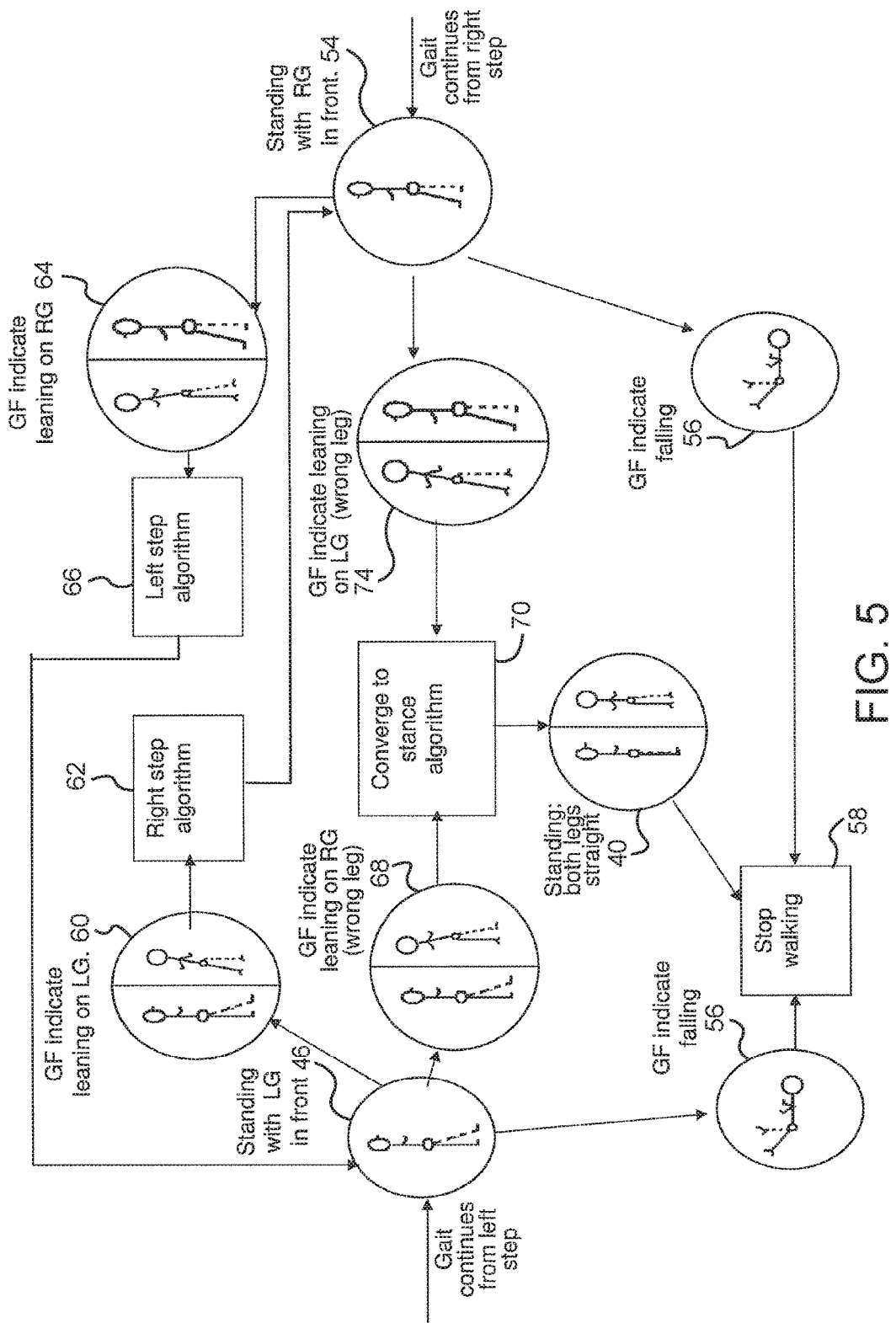
FIG. 5 is a diagram of a control process for maintaining a gait using only ground force sensors, in accordance with embodiments of the present invention.

After taking a step of the gait, with the having one leg extended (step 46 or step 54), the system again checks for tilt (step 142) and repeats the step process. If during execution of a step of the gait, the ground force sensors or a tilt sensor indicate that the user is falling (step 56), the gait maintenance process is halted (step 58). Alternatively, the process of maintaining a walking gait of the locomotion assisting exoskeleton device may be controlled by means of activating ground force sensors alone, without waiting for a signal from a tilt sensor. FIG. 5 is a diagram of the control process for maintaining a gait using only ground force sensors, in accordance with embodiments of the present invention. Leaning on the extended leg signals continuation of the gait maintenance process. If the ground force sensors do not indicate that the user has leaned on the extended leg within a predetermined period of time, the gait maintenance process times out, the legs are brought together to a standing-straight position, and the process is halted.

Figure 6:
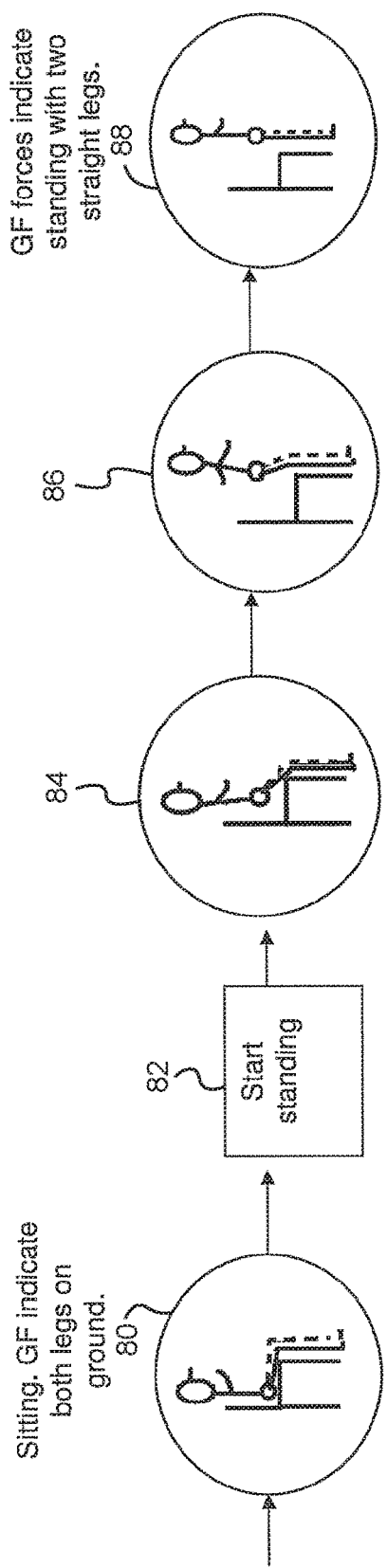
FIG. 6 is a diagram of a control process for standing from a sitting position, in accordance with embodiments of the present invention.

FIG. 6 is a diagram of the control process for standing from a sitting position, in accordance with embodiments of the present invention. The user, in a sitting position, uses the control panel unit of the locomotion assisting exoskeleton device to signal the locomotion assisting exoskeleton device that the user wishes to stand. In order to instruct the locomotion assisting exoskeleton device to initiate the standing procedure, the user places both feet on the ground (step 80, FT loading on both legs). The locomotion assisting exoskeleton device initiates a standing procedure algorithm (step 82). The locomotion assisting exoskeleton device begins straightening the user's legs (step 84 and step 86), bringing the user to a standing position (step 88). While executing the standing procedure, the locomotion assisting exoskeleton device monitors the output signals of the ground force sensors. If the standing procedure proceeds as expected, the ground force sensors measure increasing force during steps 84 and 86 until the full standing position of step 88 is attained (RFLL and LFLL loading). Alternatively or additionally, progress of the standing procedure may be monitored by means of sensors that sense the angles of the various joints, and that are incorporated in the actuation assemblies of the locomotion assisting exoskeleton device. Deviation from the expected increase in force, or change in joint angle, for a predetermined interval of time may be interpreted as indicating a problem with the standing procedure. In such a case, the locomotion assisting exoskeleton device may alert the user, and may halt or suspend the standing procedure until further instructions are received or may return the user to a sitting position 80.

Another safety means may involve a tilt sensor that senses the tilt angle of a part of the upper body of the user. If the tilt sensor indicates that the user is falling, the locomotion assisting exoskeleton device may act to attempt to prevent or mitigate the effects of the fall. For example, the locomotion assisting exoskeleton device may cause the user to sit back.

Figure 7:
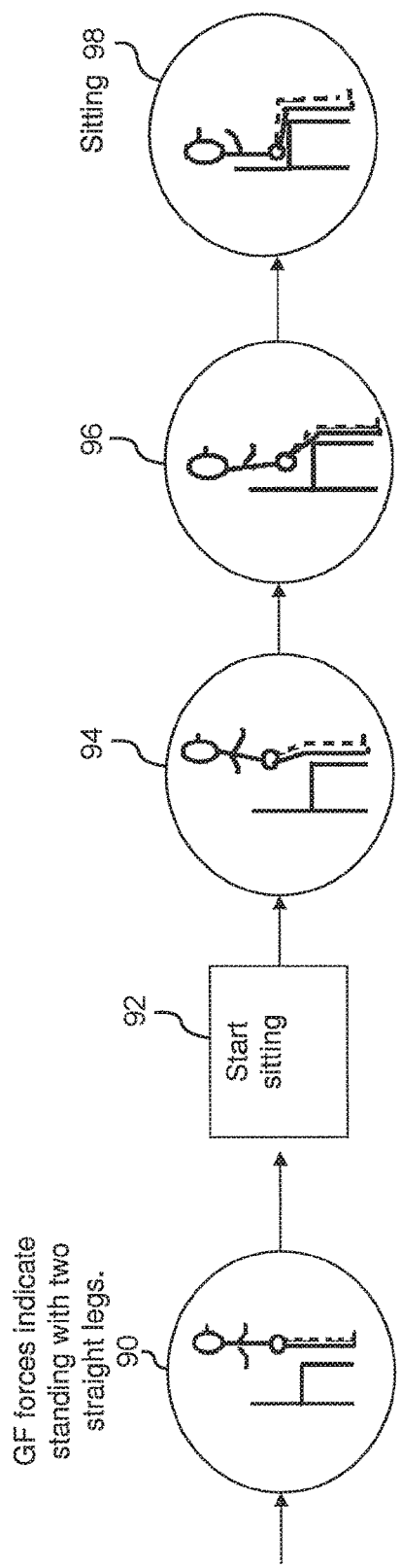
FIG. 7 is a diagram of a control process for sitting from a standing position, in accordance with embodiments of the present invention.

FIG. 7 is a diagram of the control process for sitting from a standing position, in accordance with embodiments of the present invention. While standing in front of a surface on which the user wishes to sit, the user uses the control panel unit to instruct the locomotion assisting exoskeleton device to execute a sitting procedure. The user stands straight, with approximately equal force (FLL loading) on both legs (step 90). This signals the locomotion assisting exoskeleton device to initiate a sitting procedure algorithm (step 92). The locomotion assisting exoskeleton device bends the user's legs (step 94 and step 96), bringing the user to a sitting position (step 98). While executing the sitting procedure, the locomotion assisting exoskeleton device continues to monitor the ground force sensors. It is expected that the ground force sensors will indicate decreasing ground force until a full sitting position is attained (RFT and LFT loading). Alternatively or additionally, progress of the sitting procedure may be monitored by means of sensors that sense the angles of the various joints, and that are incorporated in the actuation assemblies of the locomotion assisting exoskeleton device. A deviation from the expected decrease in force, or change in joint angle, for a predetermined interval of time may be interpreted as indicating a problem with the sitting procedure. The procedure may then be stopped or paused until further instructions are received. If a tilt sensor indicates that the user may be falling during the sitting procedure, the sitting procedure may be stopped, and action may be taken to prevent, or mitigate the effects of, the fall.

Figure 8A:
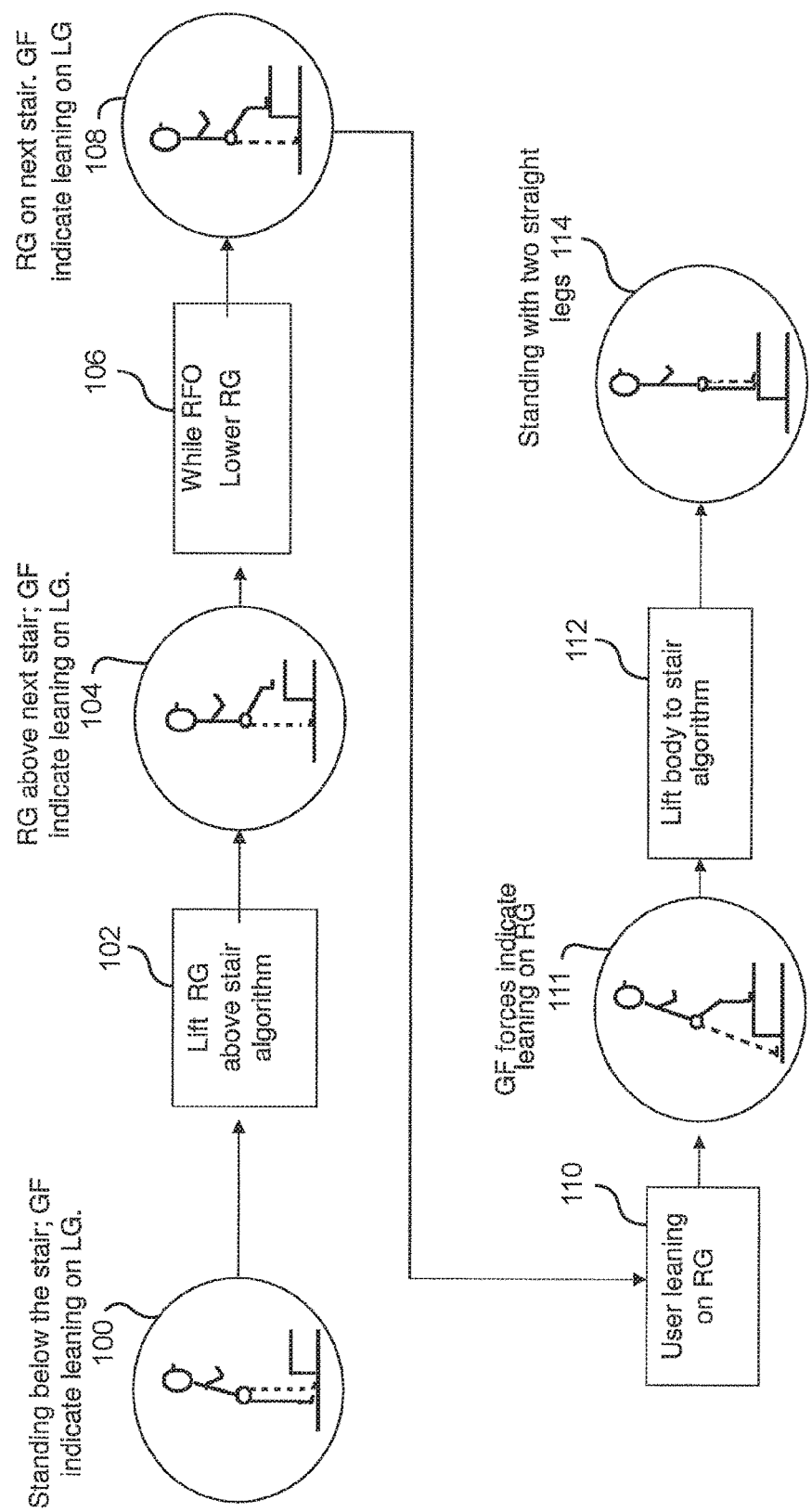
FIG. 8A is a diagram of a control process for ascending a stair, in accordance with embodiments of the present invention.
Figure 8B:
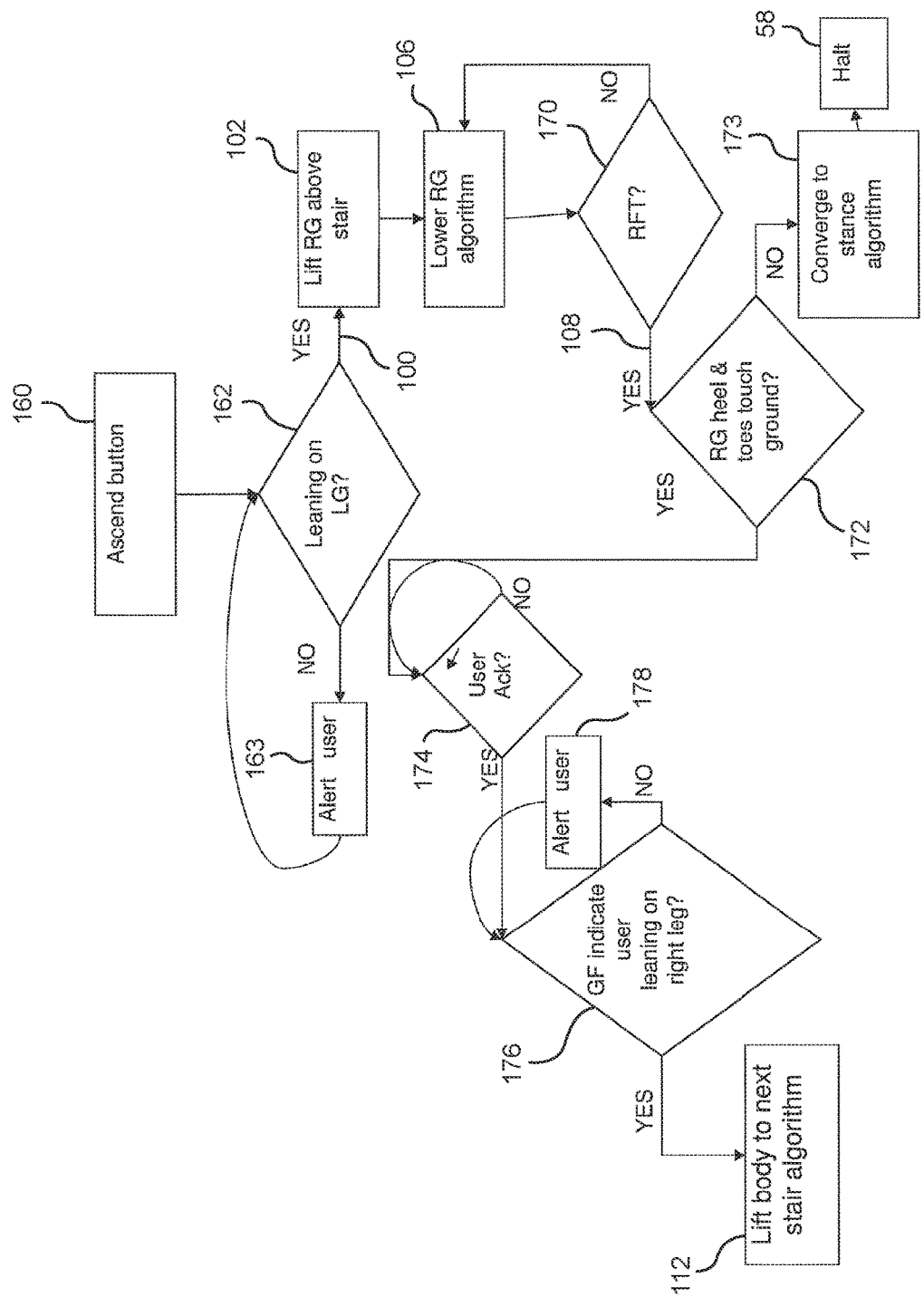
FIG. 8B is a flow chart of the control process illustrated in FIG. 8A.

FIG. 8A is a diagram of the control process for ascending a stair, in accordance with embodiments of the present invention. FIG. 8B is a flow chart of a control method for the process illustrated in FIG. 8A. To ascend a stairway of several stairs, the control process is repeated for each consecutive stair. To initiate the process of ascending a stair, a user standing below a stair to be ascended uses the control panel unit to instruct the locomotion assisting exoskeleton device to execute a stair ascending procedure (step 160). The system then checks if the ground force sensors indicate that the user is leaning on a single leg (step 162). The user leans on one leg to instruct the locomotion assisting exoskeleton device to initiate the procedure by placing the opposite leg on top of the stair. If the user does not lean on a single leg but continues to stand on both legs, the locomotion assisting exoskeleton device alerts the user (step 163).

In this example, the user leans on the left leg (step 100). For simplicity, we limit the discussion here to an example in which the user leans on the left leg in order to begin the ascent with the right leg. However, the description of the procedure remains valid if right and left legs are interchanged throughout. In response to leaning on the left leg, the locomotion assisting exoskeleton device executes an algorithm for lifting the right leg and extending it forward above the stair (step 102). With the right leg positioned above the stair, the ground force sensors are expected to indicate that the user is standing on the left leg (step 104). The locomotion assisting exoskeleton device then executes an algorithm to lower the right leg (step 106), checking the ground force sensors on the right foot brace (step 170) until the sensors indicate that the right foot has touched the top of the stair (RFT loading) while leaning on the left leg (step 108). At this point the output signals from the ground force sensors are monitored to check whether the right foot is fully resting on the stair (step 172). For example, input signals from sensors in both the toe and heel of the right foot brace may be checked to verify that all sensors indicate at least minimal contact (FT loading). If the sensor signals indicate that all or part of the right foot is not resting on top of the stair within a predetermined time interval, the algorithm assumes that the procedure has failed. In the event of such failure, the locomotion assisting exoskeleton device may return the right foot to its original position as at the beginning of the procedure (step 173), i.e. the position of step 100. The procedure is then halted until further instructions are received (step 58).

If the sensors indicate that the procedure has continued as expected, and that the right foot is fully resting on top of the stair, the locomotion assisting exoskeleton device may alert the user to this by generating an audible or other signal. For safety reasons, the locomotion assisting exoskeleton device may then await acknowledgment or verification from the user before proceeding to the next step in ascending the stair (step 174). The user may indicate verification by means of a control button, or by any other appropriate control or signaling means known in the art. Once verification is received from the user, system checks whether the user is leaning on the right leg (step 176). In addition, the system may verify that a tilt sensor indicates that the user's torso is leaning forward. If the user leans on the right leg (step 110), the system executes an algorithm to lift the left leg and the user's body to the top of the stair (step 112). Failure to lean on the right leg, or to lean forward, within a predetermined time interval may indicate the user's stance is inconsistent with safely proceeding with the ascend stair procedure. Therefore, failure to lean on the right leg, or to lean forward, may cause the locomotion assisting exoskeleton device to alert the user and to stop the procedure until further instructions are received (step 178). When step 112 is complete, the left leg is brought into line with the right leg on top of the stair. The user is then standing on top of the ascended stair (step 114). At this point, the user may use the control panel unit to instruct the locomotion assisting exoskeleton device to execute a procedure to begin a walking gait, to ascend another stair, or any other appropriate action. Throughout the stair ascending procedure, the stability and safety of the user may be achieved by concurrent use of crutches or a hand railing. During execution of the stair ascending procedure, the ground force sensors or a tilt sensor may indicate that the user is falling. The locomotion assisting exoskeleton device may then take action to prevent, or mitigate the effects of, a fall. For example, the locomotion assisting exoskeleton device may attempt to restore balance to prevent a fall, may cause the user to collapse in such a manner as to reduce the impact of a fall.

Figure 9A:
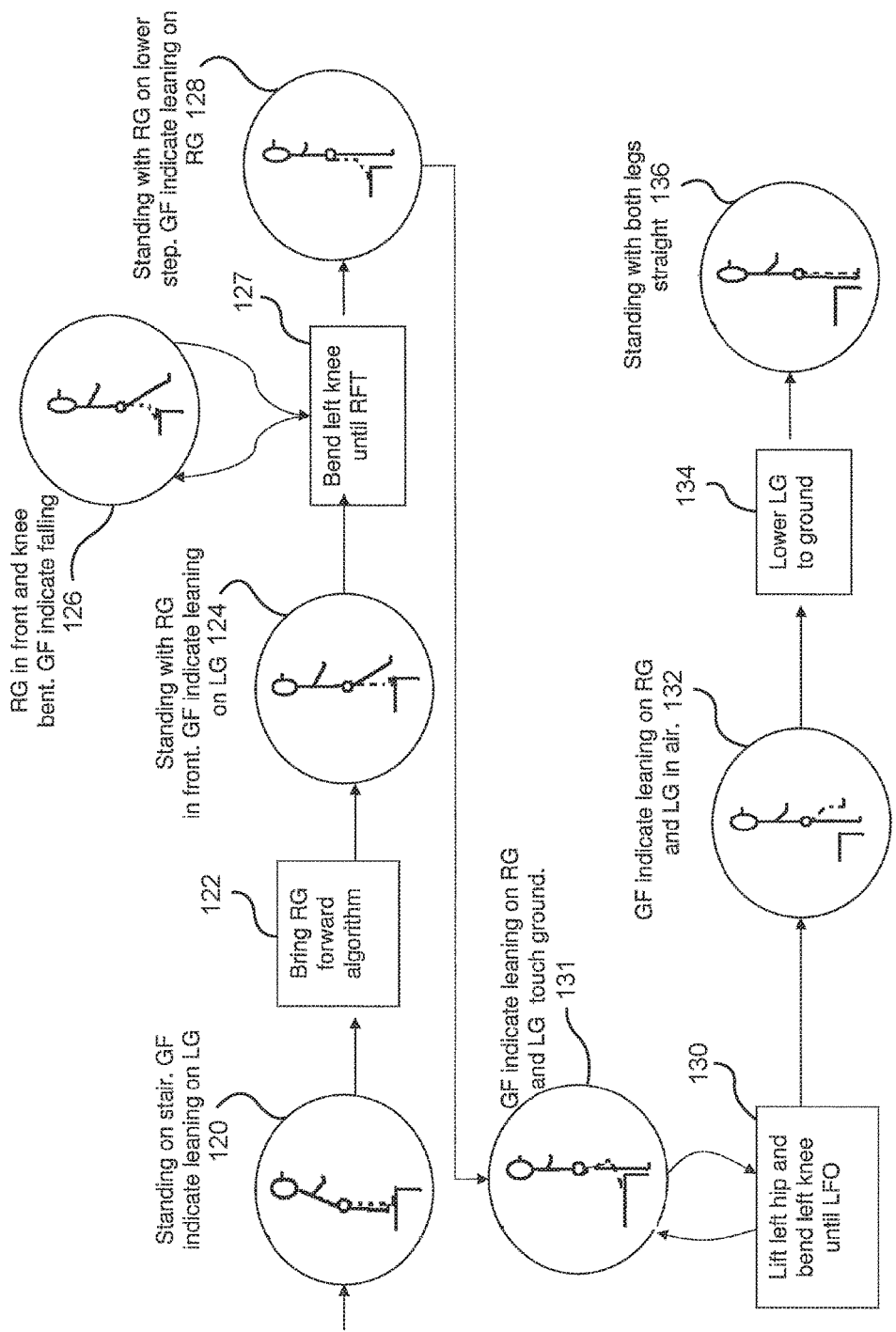
FIG. 9A is a diagram of a control process for descending a stair, in accordance with embodiments of the present invention.
Figure 9B:
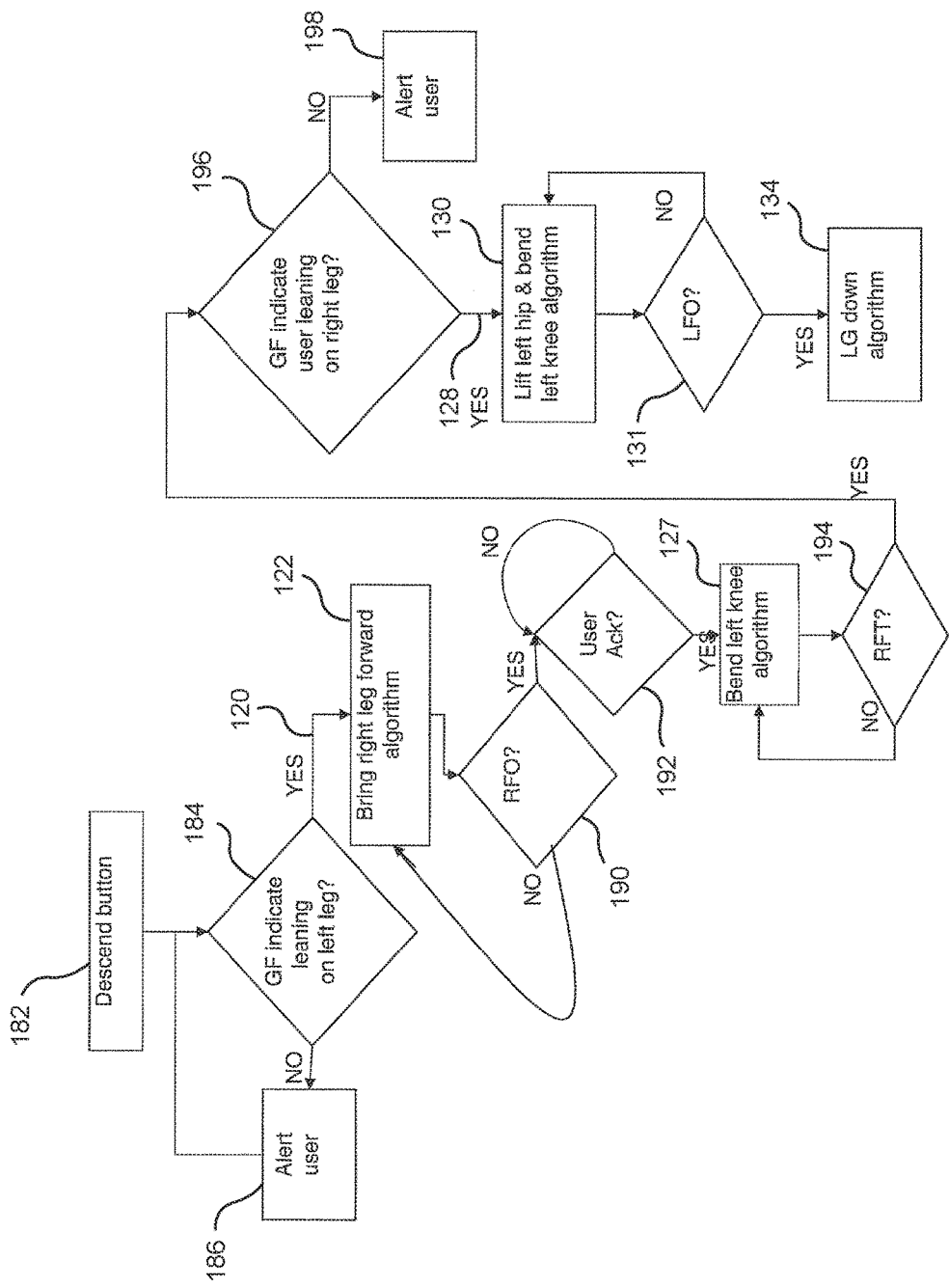
FIG. 9B is a flow chart of the process illustrated in FIG. 9A.

FIG. 9A is a diagram of the control process for descending a stair, in accordance with embodiments of the present invention. FIG. 9B is a flow chart of a control method for the process illustrated in FIG. 9A. To descend a stairway of several stairs, the control process is repeated for each consecutive stair. To initiate the process of descending a stair, a user standing on an upper level above a stair to be descended uses the control panel unit to instruct the control system of the locomotion assisting exoskeleton device to execute a stair descending procedure (step 182). The user leans on one leg to instruct the locomotion assisting exoskeleton device to initiate stair descent procedure with the opposite leg. If the user does not lean on a single leg (step 184) but continues to stand on both legs, the locomotion assisting exoskeleton device alerts the user (step 186).

In this example, the user leans on the left leg (step 120). For simplicity, we limit the discussion here to an example in which the user leans on the left leg in order to begin the descent with the right leg. However, the description remains valid if right and left legs are interchanged throughout. In response to leaning on the left leg, the system executes an algorithm for extending the right leg forward above the stair (step 122). While extending the right leg, the system continues to check if the right foot is no longer touching the upper level (RFO loading, step 190). When the right leg is extended above the stair, the ground force sensors are expected to indicate RFO loading on the right foot, and that the user is standing on the left leg (step 124). At this point, for reasons of safety, the system may wait for an acknowledgement signal indicating verification by the user (step 192). Verification from the user may be understood to indicate that crutches are properly positioned, or other precautions have been taken, to assure proper support of the user's body during the next steps of the procedure. If verification is received, the locomotion assisting exoskeleton device then executes an algorithm for bending the left knee (step 127), lowering the right leg. During execution of the algorithm of step 127, the ground force sensors may indicate a state equivalent to falling, with a combination of RFO and LFLL or LFT loading (step 126). However, in reality, the weight of the user is being supported by crutches or other means. During this phase of descending a stair, a true state of falling may be indicated only by a tilt sensor or similar sensor, and not by the ground sensors. While bending the left knee, the system checks the ground force sensors for RFT loading (step 194) that may indicate that the right foot has made contact with the top of the stair. When RFT loading is indicated, the right foot is expected to rest on the top of the stair the algorithm of step 127 ceases to execute. The ground force sensors are checked to verify that the user is leaning on the right leg (step 196). If not the user is alerted (step 198). When the user leans on the right leg (step 128), the system begins execution of an algorithm to remove the left leg from the upper level (step 130). The locomotion assisting exoskeleton device lifts the left leg at the hip and bends the left knee to remove the left foot from the upper level. This action continues as long as the ground force sensors indicate LFT loading (step 131). When the ground force sensors indicate LFO, the left foot is expected to be positioned above the stair, with the user leaning on the right leg (step 132). The system then executes an algorithm that causes the locomotion assisting exoskeleton device to lower the left foot until the left foot touches the top of the stair (step 134). When step 134 is complete, the user is standing with both legs on top of the stair (step 136). At this point, the user may use the control panel unit to instruct the locomotion assisting exoskeleton device to execute a procedure to begin a walking gait, to descend another stair, or any other appropriate action. Throughout the stair descending procedure, the stability and safety of the user may be achieved by concurrent use of crutches or a hand railing.

It should be understood that in the above descriptions of examples of control processes, steps of the processes may have been omitted for the sake of clarity and simplicity. Also, variations of the processes and procedures described above may be apparent to one skilled in the art, and are to be considered as falling within the scope of the present invention. Examples of such variations are: additional or different points during a procedure where user verification may be required, different means of indicating user verification or monitoring a procedure, additional timeout intervals that were not indicated in the above discussion, use of tilt sensor output in procedures where such use was not described in the above discussion, use of angle sensor output, changing the order of individual steps of the procedure, and other variations.

Thus, as described above, a system for the convenient, safe, and intuitive control of a locomotion assisting exoskeleton device is provided.

It should be clear that the description of the embodiments and attached Figures set forth in this specification serves only for a better understanding of the invention, without limiting its scope.

It should also be clear that a person skilled in the art, after reading the present specification could make adjustments or amendments to the attached Figures and above described embodiments that would still be covered by the present invention.

The invention claimed is:

1. A system, comprising:
a trunk support for affixing to a trunk of a person; a leg brace including at least a pair of limb segment braces; a first motorized joint adapted to provide relative angular movement between the at least pair of limb segment braces and a second motorized joint adapted to provide relative angular movement between the leg brace and the trunk support; a control panel unit configured to receive a user input and generate a signal corresponding to a locomotion mode in response to the user input, the locomotion mode including a sitting procedure and a standing procedure; a first joint sensor configured to measure a first angle of the relative angular movement between the at least pair of limb segment braces and a second joint sensor configured to measure a second angle of the relative angular movement between the leg brace and the trunk support;
a tilt sensor configured to sense a tilt angle of an upper part of the body of the person; and a controller configured to:
receive the signal from the control panel and actuate at least one of the first motorized joint and the second motorized joint to initiate the sitting procedure or the standing procedure,
receive a measurement of a change in one or both of the first angle and the second angle from one or both of the first joint sensor and the second joint sensor during the initiated procedure, respectively,
halt or suspend the initiated procedure after a predetermined time interval when a change in the received measurement deviates from an expected value,
return the person to a sitting position when the initiated procedure is a standing procedure and the tilt angle sensed by the tilt sensor indicates the person is falling.

2. The system of claim 1, wherein the controller is further configured to halt or suspend the initiated procedure when the tilt angle sensed by the tilt sensor indicates the person is falling.

3. The system of claim 1, wherein the locomotion procedure further includes an ascending procedure and a descending procedure.

4. The system of claim 1, wherein the leg brace includes a pair of leg braces, the system further comprising a crutch configured to facilitate shifting of a weight of the person between the pair of leg braces.

5. The system of claim 1, wherein the control panel unit is configured to request further instructions from the person when the initiated procedure is halted or suspended.

* * * * *